United States Patent [19]  [11] 4,209,625
Ong et al.  [45] Jun. 24, 1980

[54] SPIRO[INDOLINE-3,4'-PIPERIDINE]S

[75] Inventors: Helen H. Ong, Whippany; James A. Profitt, Somerville, both of N.J.

[73] Assignee: American Hoechst Corporation, Bridgewater, N.J.

[21] Appl. No.: 936,185

[22] Filed: Aug. 23, 1978

Related U.S. Application Data

[63] Continuation-in-part of Ser. No. 789,723, Apr. 21, 1977, abandoned.

[51] Int. Cl.² ............................................. C07D 471/10
[52] U.S. Cl. ........................................ 546/17; 424/267; 260/326.11 R; 260/326.16; 546/246; 546/215; 546/229
[58] Field of Search ............................................. 546/17

[56] References Cited

U.S. PATENT DOCUMENTS 3,299,075 1/1967 Weisbach ........................ 260/293.61

OTHER PUBLICATIONS

Kretz et al. "Helv. Chim. Acta" vol. 35 pp. 520–528 (1952).
Kornet et al. "J. Med. Chem." vol. 19, No. 7, pp. 892–898 (1976).

Primary Examiner—Henry R. Jiles
Assistant Examiner—Robert T. Bond
Attorney, Agent, or Firm—Curtis, Morris & Safford

[57] ABSTRACT

Novel spiro[indoline-3,4'-piperidine]s and related compounds and methods of preparing same are described. These compounds are useful as antidepressants, anticonvulsants and tranquilizers. Also described is a novel method of preparing indoline rings.

29 Claims, No Drawings

SPIRO[INDOLINE-3,4'-PIPERIDINE]S

This is a continuation in part of application Ser. No. 789,723 filed Apr. 21, 1977, now abandoned.

This invention relates to novel spiro[indoline-3,4'-piperidine]s and related compounds which are useful as antidepressants, anticonvulsants and tranquilizers, to methods of preparing the same, to methods of treatment with pharmaceutically effective amounts thereof, and to pharmaceutical compositions containing such compounds as essential active ingredients. These compounds are represented by the general formula:

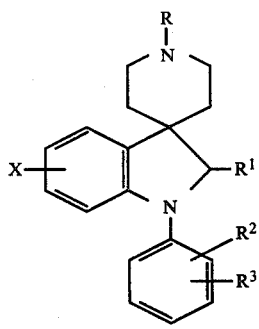

wherein R is hydrogen, loweralkyl, cyano, loweralkanoyl, phenoxycarbonyl, phenylloweralkyl, phenyllloweralkanoyl, loweralkenyl, cycloalkylloweralkyl, benzoyl,

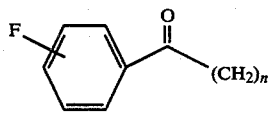

or ethylene glycol ketal of the formula

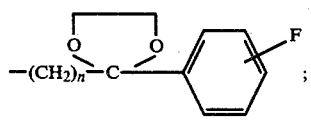

$R^1$ is hydrogen or loweralkyl; $R^2$ and $R^3$ are the same or different and each can be hydrogen, halogen, trifluoromethyl, loweralkyl, loweralkoxy, hydroxy, nitro, amino, formamido or acetamido; X is hydrogen, halogen, loweralkyl, loweralkoxy or hydroxy; and n is 1 to 4.

Physiologically acceptable salts of these compounds are included within the scope of the present invention. Also, when the term "lower" is used to modify a moiety in the above definitions, it is intended to refer to moieties of up to 4 carbon atoms and "cycloalkyl" is intended to refer to a saturated carbocyclic ring of preferably 3 to 8 carbon atoms.

To the best of our knowledge, the compounds of this invention have not heretofore been made, used, described or suggested. Although spiro-indoline and related compounds have been reported, none are known to us that have the structure disclosed in this application. To the best of our knowledge, this application discloses for the first time spiro[indoline-3,4'-piperidine]s in which the indolinyl nitrogen is substituted by an aromatic substituent. The report of Kretz, Muller and Schlittler, in Helvetica Chimica Acta, Vol. 35, pp 520-528 (1952), is believed to represent the most pertinent prior art. The indolines reported therein which are most closely related to the compounds of this invention are represented by the formula:

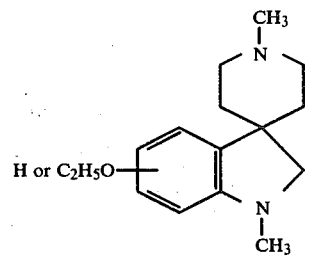

Weisbach, U.S. Pat. No. 3,299,075 entitled "Spiro[3H-Indole-3,3'-Pyrrolidine and Piperidine] Derivatives", is concerned primarily with pyrrolidines asserted to have antipyretic and analgesic activities but discloses three spiropiperidines that are distinguished from those of the present invention by the facts that they are 3,3'- rather than 3,4'-spiropiperidines and are unsubstituted in the 1-position. Kornet and Thio, in "Oxindole-3-Spiropyrrolidines and -Piperidines. Synthesis and Local Anesthetic Activity," J. Med. Chem., Vol. 19, No. 7, pp 892–898 (1976), describe the preparation of two spiro-[indolinone 3,4'-piperidine]s distinguished from the compounds of the invention by the facts that they are not substituted in the 1-position and, as the title indicates, have a keto group in the 2-position. Jansen and Richards, "Synthesis of Spiro[indoline-3,3'-pyrrolidines] Chem. Abstracts. Vol. 63, 8311, (1965) are not concerned with piperidines and do not suggest aromatic substitution of the indolino nitrogen.

The process described herein for preparing the compounds of the invention is believed to be completely new and heretofore unreported and unsuggested. As will be shown below, it involves cyclizing a molecule which already contains a piperidino moiety. Heretofore, as suggested in the aforementioned report of Kretz et al., the method or process of choice was to prepare an oxindole of the formula:

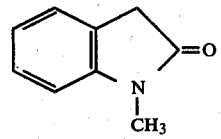

in which said oxindole bisalkylated in the presence of sodium hydride with an agent such as mechloroethamine hydrochloride to provide a spiro-oxindole of the formula:

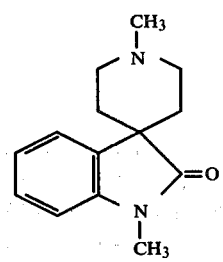

and said spiro-oxindole is reduced with lithium aluminum hydride to provide the desired spiro-indoline of the formula:

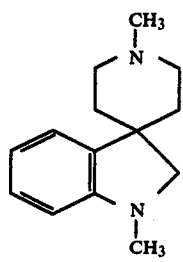

Another procedure which is described by Lyle and Skarlos in "On the Direction of Cyclization of Unsymmetrical Ketone Phenylhydrazones in the Fischer Indole Synthesis," Chem. Communications, No. 18, pp 644-646 (1966), is represented as follows:

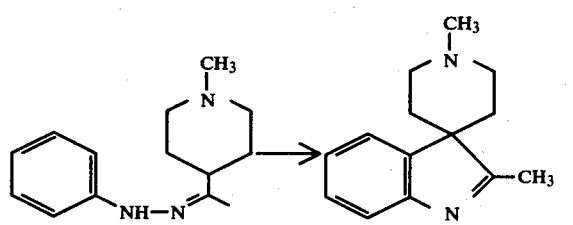

This above-depicted method is considered totally unsatisfactory because its yields of the ring system approximate only about 5%.

As will be more readily appreciated from the following detailed description of the present methodology and examples, the method of this invention differs fundamentally in strategy from the Lyle and Skarlos synthesis in that Lyle and Skarlos close an isoindole ring by formation of a C—C bond rather than a C—N bond, and the present synthesis affords excellent yields.

This aspect of ring formation through a C—N bond is not specific to the indolines of this invention but is generic with respect to all 3,3-disubstituted indolines. This constitutes an additional facet of this invention, namely a new and preferred vehicle for producing indoline rings which are depicted as follows:

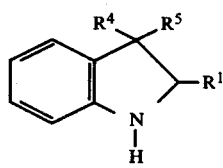

In this regard, this invention is not limited by substituents which may be present on said indoline ring.

A precursor of the compounds of the invention, a 4-cyano-4-(2-fluorophenyl)-1-methylpiperidine of the formula:

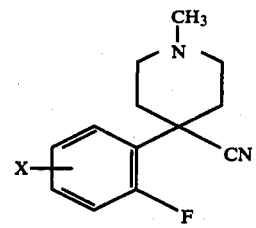

wherein X is hydrogen, halogen, loweralkoxy, or loweralkyl is prepared by the reaction of a 2-fluorophenylacetonitrile and mechloroethamine hydrochloride. The reaction is carried out in the presence of sodium hydride and a solvent such as dimethylformamide. Another precursor, a 4-imino-4-(2-fluorophenyl)-1-methylpiperidine of the formula:

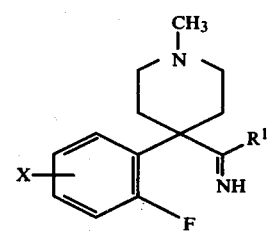

wherein R' is alkyl is prepared by the treating of an aforesaid 4-cyano-4-(2-fluorophenyl)-1-methylpiperidine via the conditions of the Grignard reaction with alkyl magnesium bromide in an ether solvent. The resulting compound is not fully hydrolyzed but treated with an aqueous saturated ammonium chloride solution leaving the imino compound as stable compound.

Any of the compounds of the invention can be prepared by one of the methods described below.

Method A

An aforesaid 4-cyano or 4-imino-4-(2-fluorophenyl)-1-methyl-piperidine is reductively cyclized to its corresponding 1'-methylspiro[indoline-3,4'-piperidine], of the formula

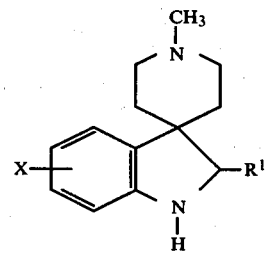

wherein $R^1$ is hydrogen, or alkyl. The cyclizing is carried out, for example, by utilizing lithium aluminum hydride as a cyclizing/reducing agent in a solvent such as 1,2-dimethoxyethane or tetrahydrofuran at a temperature of from ambient to reflux of the particular reaction mixture.

This procedure can be utilized to reduce and cyclize a compound depicted by the formula

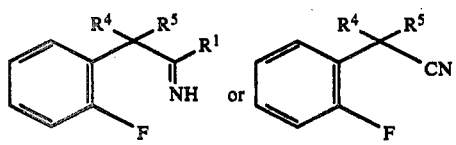

to provide a corresponding indoline ring structure, $R^4$ and $R^5$ being the same or different and each representing alkyl or aminoalkyl or, when taken together, forming a cyclic moiety.

Method B

An aforesaid 4-cyano-4-(2-fluorophenyl)-1-methylpiperidine is treated according to the conditions of the Grignard reaction with a Grignard reagent of the formula R'Mg-Y wherein R' is alkyl and Y is bromine or chlorine to produce the corresponding cyclic compound (3-H-indole) which is in turn reduced to produce a 2-alkyl or biphenyl substituted 1'-methylspiro[indoline-3,4'-piperidine], of the formula

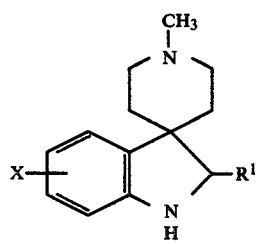

The above reduction can be carried out with sodium borohydride or lithium aluminum hydride as the reducing agent and ethanol or tetrahydrofuran, respectively, as the solvent.

Method C

A compound prepared in Method A or B can be treated with a fluorophenyl compound of the formula

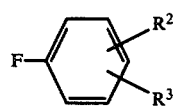

wherein $R^2$ and $R^3$ are as defined earlier except they cannot be hydroxy, amino, formamido or acetamido, in a solvent such as dimethylformamide or dimethylsulfoxide and in the presence of a base such as sodium hydride at a temperature of from ambient to the boiling point of the solvent to provide a 1-phenyl-1'-methylspiro[indoline-3,4'-piperidine], a compound of the invention of the formula

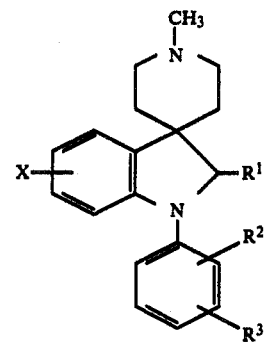

Method D

A compound of the invention wherein R is methyl prepared according to Method A, B, or C can be treated with cyanogen bromide in a solvent such as dichloromethane with an acid scavenger such as potassium carbonate at about ambient temperature to produce the corresponding compound of the invention wherein R is cyano.

Method E

A cyano compound prepared by Method D can be treated with hydrochloric acid in a water solution to cleave the cyano group, producing a compound of the invention in which R is H.

Method F

A compound prepared by Method E can be alkylated or acylated, for example, by reaction in a known manner with an alkanoylhalide or anhydride, benzoylhalide or anhydride, phenylloweralkylhalide, phenylloweralkanoylhalide, loweralkylhalide, loweralkenylhalide, cycloalkylloweralkylhalide or

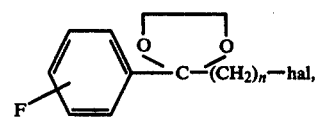

to produce the corresponding spiro[indoline-3,4'-piperidine]s substituted in the 1'-position by loweralkanoyl, benzoyl, phenylloweralkanoyl, loweralkyl, loweralkenyl, cycloalkylloweralkyl, phenylloweralkyl or

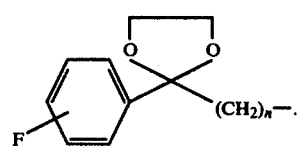

Alternatively, a compound of the invention in which R is

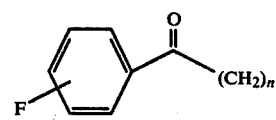

can be produced by mineral acid hydrolysis of a compound of the invention where

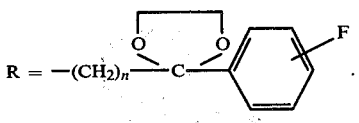

$$R = -(CH_2)_n-C\overset{O}{\underset{O}{\diagup}}\!\!\diagdown\!\!\!\!\underset{}{\bigcirc}\!\!-F$$

Method G

A 1'-acyl compound prepared in Method F can be reduced by a convenient method known to the art to produce the corresponding 1'-loweralkyl, or phenyl-loweralkyl compound, a compound of the invention. One such suitable method involves the use of lithium aluminum hydride as the reducing reagent.

Method H

A compound of the invention in which X, $R^2$ or $R^3$ is an alkoxy group prepared by any of the above methods and can be dealkylated by a method known to the art to produce the corresponding phenolic (X, $R^2$ and/or $R^3$=OH) compounds of the invention. One such method involves treatment with 48% hydrobromic acid.

Method I

A compound of the invention in which $R^2$ or $R^3$ is nitro can be reduced by a known method to give the corresponding compound of the invention in which $R^2$ or $R^3$ is amino. Such methods include catalytically reducing with a palladium on carbon catalyst or chemically reducing with zinc dust.

Method J

A compound prepared in Method I can be acylated by a known method to give the corresponding compound in which $R^2$ or $R^3$ is acetamido or formamido. One such acylation is carried out with acetic anhydride.

Acids useful for preparing the pharmaceutically acceptable acid addition salts of the invention include mineral acids such as hydrochloric, hydrobromic, sulfuric, nitric, phosphoric and perchloric acids, as well as organic acids such as tartaric, citric, acetic, succinic, maleic, fumaric and oxalic acids.

The compounds of the present invention are useful in the treatment of depression in mammals, as demonstrated by their ability to enhance the central noradrenergic and/or serotonergic nervous function. This ability was measured in rats according to the 5'-L-hydroxytryptophan Potentiation Procedure [H. Sigg, E.B., Psychiatr. Assoc. J., 4 (Suppl.); 75–85 (1959)]. In this procedure, groups of six male Wistar rats were utilized. Four hours prior to testing freshly prepared pargyline hydrochloride is subcutaneously administered. Thirty minutes before testing, drugs are intraperitoneally administered. Finally L-5-hydroxytryptophan is administered intraperitoneally and five minutes after administration the rats are observed for fifteen minutes. A compound is considered to potentiate 5-L-hydroxytryptophan activity if the rats exhibit head motion (twitching) accompanying coarse tremors. Using this test an ED50, dose effecting a 50% potentiation, is ascertained for any particular compound. For example, 1'-methyl-1-[(4-trifluoromethyl)-phenyl]spiro[indoline-3,4'-piperidine] shows an ED50 of 7.8 mg/kg. i.p. This datum illustrates that compounds of the invention are useful as antidepressants for mammals when administered in amounts ranging from about 0.1 to 50 mg/kg of body weight per day.

The usefulness of the compounds of the present invention in treatment of depression in mammals is further demonstrated by their ability to inhibit tetrabenazine-induced ptosis in mice [International Journal of Neuropharmacology, 8, 73 (1969)], a standard assay useful for evaluating antidepresant properties. Thus, for instance, 1-(2-chlorophenyl)-1'-methylspiro[indoline-3,4'-piperidine]maleate and 1-(2-fluorophenyl)-1'-methylspiro[indoline-3,4'-piperidine]maleate each effect a 50% inhibition from the ptosis of tetrabenazine-induced depression in mice at the dose of 3.2 and 4.0 mg/kg, p.o., respectively.

Compounds of the present invention are further useful as anticonvulsant agents for mammals, as determined by the method of Woodbury, L. A. and Davenport, V. D. in Arch., Int. Pharmacodynam, Vol. 92 (1952) at pp 97–107. For example, the intraperitoneal dose of 17.3 mg/kg of body weight of 1'-methyl-1-[(4-trifluoromethyl) phenyl]spiro[indoline-3,4'-piperidine] produces a 50% protection from the effect of supramaximal electro shock (SES). Similar effects are produced by the intraperitoneal doses of 10.6, 18.5, 19.2 and 38.4 mg/kg of 1-(2-fluorophenyl)-1'-methylspiro[indoline-3,4'-piperidine]maleate, 1-(4-fluorophenyl)-1'-methylspiro[indoline-3,4'-piperidine]hydrobromide, 1-(4-chlorophenyl)-1'-methylspiro[indoline-3,4'-piperidine] and 1-(2-chlorophenyl)-1'-methylspiroindoline-3,4'-piperidine]maleate, respectively. This data illustrates that compounds of the invention are useful in treating convulsions in mammals when administered in amounts ranging from about 0.1 to 50 mg/kg of body weight per day.

Compounds of the present invention are further useful as tranquilizers due to their ability to depress the central nervous system of mammals.

Compounds of this invention include:
1'-ethyl-1-(3,4-dimethylphenyl)spiro[indoline-3,4'-piperidine];
1'-methyl-6-methoxy-1-phenylspiro[indoline-3,4'-piperidine];
5-fluoro-1-(4-chlorophenyl)-1'-phenylethylspiro[indoline-3,4'-piperidine];
1-(3-methoxyphenyl)spiro[indoline-3,4'-piperidine];
1-(3-hydroxyphenyl)spiro[indoline-3,4'-piperidine];
1'-phenylacetyl-1-phenylspiro[indoline-3,4'-piperidine];
1'-benzyl-1-phenylspiro[indoline-3,4'-piperidine];
1'-cyclopropylmethyl-1-(3-methoxyphenyl)spiro[indoline-3,4'-piperidine];
1'-allyl-1-(3-chlorophenyl)spiro[indoline-3,4'-piperidine];
1'-methyl-6-methyl-1-phenylspiro[indoline-3,4'-piperidine];
1-(2,4-diaminophenyl)-1'-methylspiro[indoline-3,4'-piperidine];
1-(3-chloro-2-methylphenyl)-1'-methylspiro[indoline-3,4'-piperidine];
1-(5-chloro-2-methylphenyl)-1'-methylspiro[indoline-3,4'-piperidine];
1-(2-nitro-4-chlorophenyl)-1'-methylspiro[indoline-3,4'-piperidine]; and
1'-(4-fluorobenzoylmethyl-1-phenylspiro[indoline-3,4'-piperidine].
1'-methyl-6-hydroxy-1-phenylspiro[indoline-3,4'-piperidine]

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The invention is further illustrated by the following examples:

EXAMPLE 1 a. A solution of 14.9 g of 2-fluorophenylacetonitrile in 250 ml of dimethylformamide is added with vigorous stirring over a 5 minute span to 9.6 g of 99% sodium hydride. After total addition the reaction mixture is allowed to stand for 30 minutes at ambient temperature before a solution of 19.3 g of mechloroethamine hydrochloride in dimethylformamide is added dropwise. After total addition the reaction mixture is stirred at 90°–95° C. for 16 hours, leaving a very dark suspension. The suspension is poured onto ice water and the organic phase is extracted four times with 50 ml portions of ether. The combined extracts are shaken with an excess of 2 N HCl and the acidic extract is collected. The acidic solution is basified with cold ammonia leaving an oily amine which crystallizes with chilling. The solid is collected and recrystallized from hexane to give off-white crystals, mp 69°–71° C., of 4-cyano-4-(2-fluorophenyl)-1-methylpiperidine. Infrared and nuclear magnetic resonance spectra confirm this structure.

b. A solution of 3.3 g of 4-cyano-4-(2-fluorophenyl)-1-methylpiperidine in 20 ml of 1,2-dimethoxyethane is added dropwise to a refluxing slurry of 800 mg of lithium aluminum hydride in 1,2-dimethoxyethane. After total addition the mixture is stirred at reflux for 64 hours and decomposed with successive portions of water, dilute sodium hydroxide and water. The granular aluminum oxide produced is filtered off and the filtrate is extracted thrice with hot chloroform. The combined organic solution is washed with water and dried. The solvent is removed in vacuo leaving a thick oil which crystallizes on standing. The product is recrystallized from a benzene-hexane mixture to give prisms, mp 135°–137° C., of 1'-methylspiro[indoline-3,4'-piperidine].

c. A mixture of 0.9 g of 1'-methylspiro[indoline-3,4'-piperidine], 2 g of 4-fluorobenzotrifluoride and 0.25 g of 50% sodium hydride in 20 ml of dimethylformamide is stirred under nitrogen at a temperature of 95° C. for two hours. The mixture is allowed to cool, diluted with water and then extracted three times with 100 ml portions of ether. The combined ether extracts are back extracted with an excess of 2 N hydrochloric acid. The acidic solution is basified with potassium carbonate to effect a product which is eluted with a 25% methanol in benzene mixture through a silica gel column to give a pale yellowish oil which crystallizes with cooling. Recrystallization of these crystals from hexane gives rhombic crystals, mp 122°–124° C., of 1'-methyl-1-(4-trifluoromethylphenyl)spiro[indoline-3,4'-piperidine].

Analysis: Calculated for $C_{20}H_{21}F_3N_2$: 69.34%C; 6.11%H; 8.08%N; 16.45%F. Found: 69.60%C; 6.25%H; 7.97%N; 16.25%F.

EXAMPLE 2

By following the procedures of Example 1, substituting 4-chlorofluorobenzene for 4-fluorobenzotrifluoride produces pale yellowish crystals which are recrystallized from an ether-hexane mixture to give the product, mp 123°–125° C., of 1-(4-chlorophenyl)-1'-methylspiro[indoline-3,4'-piperidine].

Analysis: Calculated for $C_{19}H_{21}ClN_2$: 72.95%C; 6.77%H; 8.96%N; 11.33%Cl. Found: 73.05%C; 6.70%H; 9.16%N; 11.36%Cl.

EXAMPLE 3

A mixture of 0.95 g of 1-(4-chlorophenyl)-1'-methylspiro[indoline-3,4'-piperidine] (Example 2), 0.42 g of cyanogen bromide and 1 g of potassium carbonate in 25 ml of dichloromethane is stirred at ambient temperature for two hours. The reaction mixture is filtered and the filtrate concentrated to dryness leaving an oily residue which is crystallized from an acetone-hexane mixture leaving colorless crystals, mp 178.5°–180° C., of 1-(4-chlorophenyl)-1'-cyanospiro[indoline-3,4'-piperidine].

Analysis: Calculated for $C_{19}H_{18}ClN_3$: 70.47%C; 5.60%H; 12.98%N. Found: 70.30%C; 5.68%H; 13.03%N.

EXAMPLE 4

A mixture of 1.6 g of 1'-methylspiro[indoline-3,4'-piperidine] (Example 1b), 2.0 g of 50% sodium hydride and 3 ml of 3-fluorobenzotrifluoride in 15 ml of dimethyl sulfoxide is stirred at ambient temperature for one hour and then poured onto ice. The biphasic mixture is extracted thrice with 100 ml portions of ether. The ether extracts are combined and dried and treated with hydrogen chloride to produce the salt. The solvent is decanted off, leaving a gummy salt which is basified with dilute ammonium hydroxide. The solvent is removed under reduced pressure, leaving a yellowish oil which solidifies on standing. The solid is recrystallized from pentane, leaving yellow colored needles, mp 123°–124.5° C., of 1-(3-trifluoromethylphenyl)-1'-methylspiro[indoline-3,4'-piperidine].

Analysis: Calculated for $C_{20}H_{21}F_3N_2$: 69.34%C; 6.11%H; 8.08%N; 16.45%F. Found: 69.52%C; 6.18%H; 8.00%N; 16.26%F.

EXAMPLE 5

A mixture of 5.8 g of 1'-methylspiro[indoline-3,4'-piperidine] (Example 1b), 5.0 g of 50% sodium hydride and 12 ml. of 1,4-difluorobenzene in 50 ml of dimethyl sulfoxide is stirred at 55°–60° C. for one hour. The mixture is permitted to cool and then diluted with water and extracted thrice with 100 ml portions of ether. The ether extracts are extracted with an excess of 3 N hydrochloric acid and the acidic solution is basified leaving an oil which is dissolved in ether and dried. The ether is removed under reduced pressure, leaving a yellowish oil. The oil is eluted with a 10% methanolic methylene chloride mixture through a silica gel column packed in methylene chloride and then converted to a crystalline hydrobromide. The salt is recrystallized from a methanol-acetone-ether mixture, producing off-white granules, mp 267°–269° C., of 1-(4-fluorophenyl)-1'-methylspiro[indoline-3,4'-piperidine] hydrobromide.

Analysis: Calculated for $C_{19}H_{21}FN_2 \cdot HBr$: 60.48%C; 5.96%H; 7.43%N. Found: 60.32%C; 5.88%H; 7.28%N.

EXAMPLE 6

A solution of 0.42 g of 1-(4-fluorophenyl)-1'-methylspiro[indoline-3,4'-piperidine], the free base of Example 5, in 2 ml of chloroform is added dropwise to a refluxing mixture of 0.2 of cyanogen bromide and 0.4 g of potassium carbonate in 8 ml of chloroform. After total addition, the reaction mixture is stirred at ambient temperature for 16 hours and then filtered. The solvent is removed under reduced pressure, leaving a viscous oil which crystallizes on standing. These crystals are recrystallized from an acetone-hexane mixture to give off-white prisms, mp 139°–140° C., of 1'-cyano-1-(4-fluorophenyl)spiro[indoline-3,4'-piperidine]. Analysis: Calculated for $C_{19}H_{18}FN_3$: 74.23%C; 5.90%H; 13.67%N. Found: 74.30%C; 5.93%H; 13.70%N.

EXAMPLE 7

A mixture of 2.1 g of 1'-methylspiro[indoline-3,4'-piperidine] (Example 1b), 3 g of 50% sodium hydride and 12 ml of fluorobenzene in 18 ml of dimethyl sulfoxide is stirred at 65°-70° C. for 45 hours. The well stirred mixture is poured into water and extracted thrice with ether. The combined ether extracts are dried briefly before forming the hydrochloride salt. The salt is collected, basified and then extracted into ether, giving a yellowish oil which is crystallized from hexane, producing off-white crystals, mp 90°–92° C. of 1'-methyl-1-phenylspiro[indoline-3,4'-piperidine].

Analysis: Calculated for $C_{19}H_{22}N_2$: 81.96%C; 7.97%H; 10.06%N. Found: 82.07%C; 8.09%H; 9.98%N.

EXAMPLE 8

A mixture of 0.5 g of 1'-methyl-1-phenylspiro[indoline-3,4'-piperidine] (Example 7), 0.5 g of potassium carbonate and 0.2 g of cyanogen bromide in 10 ml of methylene chloride is stirred at ambient temperature for two hours. The stirred mixture is filtered and the filtrate evaporated to dryness under reduced pressure. Eluting the residue with chloroform through a silica gel column packed in chloroform provides colorless crystals which are recrystallized from an acetone-hexane mixture to give fine granules, mp 136°–138° C., of 1'-cyano-1-phenylspiro[indoline-3,4'-piperidine].

Analysis: Calculated for $C_{19}H_{19}N_3$: 78.85%C; 6.62%H; 14.52%N. Found: 78.66%C; 6.53%H; 14.30%N.

EXAMPLE 9 a. A solution of 4.4 g of 4-cyano-4-(2-fluorophenyl)-1-methylpiperidine (Example 1a), in 30 ml of sieve-dried 1,2-dimethoxyethane is added dropwise to a solution of 3 M ethylmagnesium bromide in ether. After total addition the reaction mixture is stirred at a temperature of 80° C. for 16 hours. The mixture is then decomposed with an excess of a saturated aqueous ammonium chloride solution and the organic phase is extracted with ether. The combined ether extracts are dried and the solvent is removed, leaving a crude residue. The residue is purified by eluting from an alumina column with ether, leaving a yellowish oil which is treated with a solution of 0.75 g of sodium borohydride in 15 ml of ethanol for 16 hours. The resulting product is converted, in ether, to its dihydrobromide salt, which is recrystallized from methanol to give yellowish prisms, mp 250° C., of 2-ethyl-1'-methylspiro[indoline-3,4'-piperidine] dihydrobromide.

b. By following the procedure of Example 1c, 2-ethyl-1'-methylspiro[indoline-3,4'-piperidine], the free base of part a, is treated with 4-chlorofluorobenzene to yield 1-(4-chlorophenyl)-2-ethyl-1'-methylspiro[indoline-3,4'-piperidine].

EXAMPLE 10

A reaction mixture of 2.6 g of 1'-methylspiro[indoline-3,4'-piperidine] (Example 1b), 0.32 g of 98% sodium hydride and 2.8 ml of o-difluorobenzene in 20 ml of dimethyl sulfoxide is stirred at 55° C. for ten minutes and then poured into a solution of 0.33 g of 98% sodium hydride with the reaction maintained at 55° C. for an additional 60 minutes. The reaction mixture is then poured into 300 ml of ice-water and the biphasic mixture extracted thrice with 100 ml portions of ether. The combined ether extracts are successively washed twice with 100 ml portions of water and extracted twice with 60 ml portions of 3 N hydrochloric acid. The acidic solution is basified to a pH of 10 with ammonia. The alkaline mixture is extracted twice with 100 ml portions of ether. The combined ether extracts are washed successively with a 100 ml portion of water and a 30 ml portion of a saturated sodium chloride solution and dried, leaving an oil. The oil is eluted through a silica gel column with a 5% methanol and then is dissolved in ether, where it is converted to its maleic acid salt. The salt is recrystallized from an acetone-ether mixture to give a white crystalline material, mp 209°–210° C., of 1-(2-fluorophenyl)-1'-methylspiro[indoline-3,4'-piperidine]maleate.

Analysis: Calculated for $C_{19}H_{21}FN_2 \cdot C_4H_4O_4$: 66.97%C; 6.11%H; 6.79%N; 4.61%F. Found: 66.70%C; 6.19%H; 6.87%N; 4.40%F.

EXAMPLE 11

A mixture of 1'-cyano-1-phenylspiro[indoline-3,4'-piperidine] (Example 8), is treated with 3 N hydrochloric acid to provide 1-phenylspiro[indoline-3,4'-piperidine].

EXAMPLE 12

A mixture of 1-phenylspiro[indoline-3,4'-piperidine] (Example 11), propionyl chloride and sodium bicarbonate in chloroform is stirred at reflux. The mixture is permitted to cool, filtered, and the filtrate concentrated, leaving 1-phenyl-1'-propionylspiro[indoline-3,4'-piperidine]. In a similar fashion, 1-phenylspiro[indoline-3,4'-piperidine] is treated with benzoylchloride to provide 1'-benzoyl-1-phenylspiro[indoline-3,4'-piperidine].

EXAMPLE 13

A solution of 1-phenyl-1'-propionylspiro[indoline-3,4'-piperidine] (Example 12), in tetrahydrofuran is added dropwise to a stirred suspension of lithium aluminum hydride in tetrahydrofuran. The mixture is heated under reflux for two hours, cooled, quenched cautiously with water and extracted with ether. The ether solution is dried and concentrated to the solid, 1-phenyl-1'-n-propylspiro[indoline-3,4'-piperidine].

EXAMPLE 14

A solution of 5.0 g of 1'-cyano-1-(4-fluorophenyl)-spiro[indoline-3,4'-piperidine] (Example 6), in 100 ml of tetrahydrofuran is added dropwise to a refluxing mixture of 3 g of lithium aluminum hydride in 100 ml of tetrahydrofuran. After total addition, the reaction mixture is stirred at reflux for three hours and then decomposed with water and dilute sodium hydroxide. The resulting oily product is converted to a crystallized from a methanol-acetone-ether mixture leaving off-white prisms, mp 185°–188° C., of 1-(4-fluorophenyl)-spiro[indoline-3,4'-piperidine]maleate.

Analysis: Calculated for $C_{18}H_{19}FN_2 \cdot C_4H_4O_4$: 66.32%C; 5.82%H; 7.03%N. Found: 66.19%C; 5.92%H; 6.96%N.

EXAMPLE 15

A reaction mixture of 12.4 g of 1'-methylspiro]indoline-3,4'-piperidine] (Example 1b), and 17.2 g of o-fluoronitrobenzene is maintained at a temperature of from 170°–175° C. under nitrogen for five hours. The resulting product solidifies at ambient temperature. The solid is pulverized and triturated with 350 ml of an ether-hexane (1:4) mixture, collected by filtration through a course sintered glass funnel and air dried. The dried product is dissolved in chloroform and treated portionwise with 9.7 ml of triethylamine, leaving a slurry. The slurry is poured into water and the organic phase collected and filtered. The filtrate is collected, washed with chloroform and the combined organic solutions are, successively, washed twice with water, dried and concentrated to dryness. The resulting residue is recrystallized from hot isopropyl ether, leaving the pure product, mp 132°–132.5° C., of 1-(2-nitrophenyl)-1'-methylspiro[indoline-3,4'-piperidine].

Analysis: Calculated for $C_{19}H_{21}N_3O_2$: 70.57%C; 6.54%H; 12.99%N. Found: 70.80%C; 6.75%H; 12.99%N.

EXAMPLE 16

A large excess, about 20–25 g, of zinc dust is added portionwise to a vigorously stirring solution, at about 0° C., of 10.7 g of 1-(2-nitrophenyl)-1'-methylspiro[indoline-3,4'-piperidine] Example 15), in a combined solvent of 75 ml of ethanol and 5 ml of concentrated hydrochloric acid. After total addition, an additional 15 ml of concentrated hydrochloric acid is carefully added to maintain the temperature of the reaction mixture below 70° C. The reaction mixture is basified with concentrated ammonia, and the alkaline mixture is filtered and concentrated to dryness. The residue is partitioned between 400 ml of methylene dichloride and 400 ml of 10% sodium hydroxide. The organic portion is successively washed thrice with 400 ml portions of 10% sodium hydroxide and then once with a 400 ml portion of water, dried and concentrated to dryness, leaving a black glassy product. The product is converted to its hydrochloride in ether which is recrystallized from a methanol-ether mixture to leave the salt, mp 243° C., dec, of 1-(2-aminophenyl)-1'-methylspiro[indoline-3,4'-piperidine]dihydrochloride.

Analysis: Calculated for $C_{19}H_{23}N_2 \cdot 2HCl$: 62.30%C; 6.89%H; 11.47%N. Found: 62.40%C; 6.96%H; 11.41%N.

EXAMPLE 17

Ice water is added to a mixture of 1.8 g of 1'-methylspiro[indoline-3,4'-piperidine] (Example 1b), 1.5 ml of 2-chlorofluorobenzene, 1.0 g of sodium hydride in 30 ml of dimethylsulfoxide which was stirred at 50° C. under nitrogen for one hour. The biphasic mixture is extracted thrice with ether and the combined ether extracts are shaken with a large excess of 2 N hydrochloric acid. The neutral fraction is discarded and the acidic solution basified, leaving an oil. The oil is dissolved in ether, dried and converted to a crystalline maleate which is recrystallized from an ethanol-ether mixture to give off-white crystals, mp 178.5°–179° C. of 1-(2-chlorophenyl)-1'-methylspiro-[indoline-3,4'-piperidine]maleate.

Analysis: Calculated for $C_{19}H_{21}ClN_2 \cdot C_4H_4O_4$: 64.40%C; 5.88%H; 6.53%N; 8.27%Cl. Found: 64.41%C; 6.00%H; 6.35%N; 8.22%Cl.

EXAMPLE 18 a. A solution of 4.4 g of 2,5-difluorobenzenyl cyanide in 50 ml of dimethylsulfoxide is carefully added to 2.9 g of 98% sodium hydride. After total addition, the solution is permitted to stand at ambient temperature for 45 minutes before 5.0 g of mechlorethamine hydrochloride in 50 ml of dimethylsulfoxide are added over a 30 minute span. After total addition, the mixture is stirred at 70° C. for one hour and permitted to stand at ambient temperature for 16 hours. The mixture is diluted with water and the reaction mixture is extracted thrice with ether and the combined ether extracts are shaken with an excess of 2 N hydrochloric acid. The acidic solution is basified with concentrated ammonia, liberating a crude product. The product is chromatographed through a silica gel column with an eluant of 10% methanol in methylene dichloride. The major fraction, a colorless oil (Rf 0.4) is converted to a crystalline maleate in ether. The salt is recrystallized from an acetone-ether mixture to give colorless crystals, mp 209°–211° C., of 4-cyano-4-(2,5-difluorophenyl)-1-methylpiperidine maleate.

Analysis: Calculated for $C_{13}H_{14}F_2N_2 \cdot C_4H_4O_4$: 57.95%C; 5.15%H; 7.95%N; 10.79%F. Found: 58.06%C; 5.14%H; 7.89%N; 10.50%F.

b. A sample of 4-cyano-4-(2,5-difluorophenyl)-1-methyl-piperidine, free base of a, is treated in accordance with the procedure of Example 1 b, to provide 5-fluoro-1'-methylspiro[indoline-3,4'-piperidine].

EXAMPLE 19

A sample of 5-fluoro-1'-methylspiro[indoline-3,4'-piperidine], Example 18 b, is treated in accordance with the procedure of Example 7, to provide 5-fluoro-1'-methyl-1-phenylspiro[indoline-3,4'-piperidine].

EXAMPLE 20

A mixture of 2.5 g of 1-(4-fluorophenyl)spiro[indoline-3,4'-piperidine], free base of Example 14, 2.4 g of 4-chloro-4-fluorobutyrophenone ethylene ketal, 1.8 g of sodium bicarbonate, 1.8 g of potassium iodide in 25 ml of dimethylformamide is stirred at 80° C. for 16 hours. Thereafter, the mixture is diluted with methylene chloride and then filtered. The filtrate is concentrated leaving as a reddish oil, the compound 1'-[3-(4-fluorobenzoyl)propyl]1-(4-fluorophenyl)spiro[indoline-3,4'-piperidine] ethylene glycol ketal. The oil is hydrolyzed with a mixture of 25 ml of 3 N hydrochloric acid and 40 ml of ethanol and the acidic solution is basified with 40% sodium hydroxide. The liberated amine is dissolved in a methylene chloride ether (1:1) mixture and then this solvent is evaporated off. The amine is purified by passing through an alumina column, ether eluant, providing a yellowish oil. The oil, in ether, is converted to its maleic acid salt which is recrystallized from a methyl alcohol-ether mixture to provide off-white crystals, mp 181°–183° C., of 1'-[3-(4-fluorobenzoyl)propyl]-1-(4-fluorophenyl)spiro[indoline-3,4'-piperidine]maleate.

Analysis: Calculated for $C_{28}H_{28}F_2N_2O \cdot C_4H_4O_4$: 68.31%C; 5.73%H; 4.98%N; 6.75%F. Found: 68.10%C; 5.58%H; 4.64%N; 6.48%F.

EXAMPLE 21

A mixture of 0.82 g of 1-(2-fluorophenyl)-1'-methylspiro-[indoline-3,4'-piperidine], free base of Example 10, 0.92 g of cyanogen bromide and 1.0 g of potassium carbonate in 24 ml of methylene dichloride is stirred at ambient temperature for 5 hours and then an additional 0.20 g of cyanogen bromide is added. Stirring is continued for 16 hours before filtering the mixture. The filtrate is boiled with methyl alcohol and the hot solution is evaporated to dryness leaving a brown foam. This product is purified by passing through a silica gel column, ether methylene chloride (1:1) mixture eluant, to provide a tan solid. The solid is recrystallized from an acetone-hexane mixture to provide white needles (slight tan tint), mp 131°–132° C. of 1'-cyano-1-(2-fluorophenyl)spiro[indoline-3,4'-piperidine].

Analysis: Calculated for $C_{19}H_{18}FN_3$: 74.24%C; 5.90%H; 13.67%N. Found: 74.20%C; 5.96%H; 13.71%N.

EXAMPLE 22

To an ice cold slurry of 6.81 g of 1-(2-aminophenyl)-1'-methylspiro[indoline-3,4'-piperidine] dihydrochloride, Example 16, in 100 ml of methylene chloride is added dropwise a solution of 8.4 ml of triethylamine in 50 ml of methylene chloride. After total addition a solution of 1.5 ml of acetyl chloride in 50 ml of methylene chloride is added dropwise to the reaction mixture and then same is stirred for 16 hours. Thereafter, the mixture is sequentially washed with 2200 ml portions of water, washed once with a 200 ml portion of a 10% aqueous sodium hydroxide solution, washed once with a 200 ml portion of water, washed once with a 200 ml portion of brine, dried and concentrated. The residue is dissolved in 50 ml of ether and the solution is stirred vigorously and then filtered. To the filtered solution is added an ethereal solution of oxalic acid effecting a salt as a precipitate, 200 ml of ether are added and the salt is collected by filtration. The salt is recrystallized from hot isopropyl alcohol leaving the product, mp 170° C., dec., of 1-(2-acetylaminophenyl)-1'-methylspiro[indoline-3,4'-piperidine] oxalate.

Analysis: Calculated for $C_{21}H_{25}N_3O \cdot C_2H_2O_4$: 64.93%C; 6.40%H; 9.88%N. Found: 64.73%C; 6.34%H; 9.91%N.

EXAMPLE 23 a. A solution of 8.5 g of 4-chloro-2-fluorobenzyl nitrile in 100 ml of dimethylsulfoxide is added portionwise over a 5 minute span to 4.4 g of sodium hydride (99%). After total addition, the mixture is stirred at ambient temperature for 30 minutes before the dropwise addition of a solution of 8.5 g of mechlorethamine hydrochloride in 100 ml of dimethylsulfoxide. After total addition the mixture is stirred at 75° C. for 1 hour and then at ambient temperature for 30 minutes. The resulting dark suspension is poured into ice-water and the biphasic mixture is extracted with ether, the other extracts are treated with an excess of 2 N hydrochloric acid precipitating a salt, the salt is collected by filtration and then sequentially washed with ether and basified with ammonium hydroxide. The alkaline solution is extracted with ether and the ether extracts are dried and then concentrated under vacuum leaving a heavy yellowish oil which crystallizes upon cooling. The product is recrystallized from an ether-pentane mixture to provide rhombic crystals, mp 85°–87° C. of 4-(4-chloro-2-fluorophenyl)-4-cyano-1-methylpiperidine.

b. To a refluxing suspension of lithium triethoxyaluminum hydride (prepared by dropping 12 ml of absolute ethyl alcohol carefully into a cooled slurry of 4.9 g of lithium aluminumhydride in 150 ml of glyme) is added over a 30 minute span a mixture of 8.1 g of 4-(4-chloro-2-fluorophenyl)-4-cyano-1-methylpiperidine in 80 ml of glyme. After total addition, stirring is continued at reflux for 72 hours. Thereafter, the mixture is permitted to cool before successively adding 5 ml of water, 5 ml of a 15% aqueous sodium hydroxide solution and 15 ml of water effecting a precipitate. The precipitate is collected by filtration followed by repeated washings with warm methylene chloride. The filtrate, combined with the washings, is successively washed with water, dried and evaporated to dryness leaving a white crystalline solid. The solid is recrystallized from an acetone-pentane mixture to provide fine needles, mp 172°–173° C. of 6-chloro-1'-methylspiro[indoline-3,4'-piperidine].

c. A mixture of 2.4 g of 6-chloro-1'-methylspiro[indoline-3,4'-piperidine], 0.5 g of sodium hydride and 6 g of 2-fluorobenzotrifluoride in 30 ml of dimethylsulfoxide is stirred under nitrogen for 30 minutes. An exothermic reaction occurs during this time. Thereafter, the mixture is diluted with water, and the diluted mixture thrice with ether. The combined ether extracts are extracted with 2 N hydrochloric acid. The acidic extracts are basified providing a colorless oil. The oil is dissolved in ether and the solution is dried. The product is passed through an alumina column, ether eluant, to provide a colorless oil which is converted, in ether, to its maleic acid salt. The salt is recrystallized from an acetone-ether mixture to provide white platelets, mp 209°–211° C. of 6-chloro-1-(2-trifluoromethylphenyl)-1'-methylspiro[indoline-3,4'-piperidine] maleate.

Analysis: Calculated for $C_{20}H_{20}ClF_3N_2 \cdot C_4H_4O_4$: 58.00%C; 4.87%H; 5.64%N; 11.47%F. Found: 58.26%C; 4.68%H; 5.63%N; 11.23%F.

EXAMPLE 24

A mixture of 0.5 g of 6-chloro-1-(2-trifluoromethylphenyl)-1'-methylspiro[indoline-3,4'-piperidine)], free base of Example 23, 0.3 g of cyanogen bromide, 1.0 g of potassium carbonate in 20 ml of methylene chloride is stirred at ambient temperature for 4 hours. Thereafter, the mixture is filtered and the filtrate is concentrated leaving a semi-solid residue. The residue is recrystallized from an acetone-hexane mixture to rovide white prisms, mp 153°–154.5° C. of 6-chloro-1'-cyano-1'-(2-trifluoromethylphenyl)spiro[indoline-3,4'-piperidine].

Analysis: Calculated for $C_{20}H_{17}ClF_3N_2$: 61.30%C; 4.37%H; 10.72%N. Found: 61.45%C; 4.22%H; 10.77%N.

EXAMPLE 25

A mixture of 6.3 g of 6-chloro-1'-methylspiro[indoline-3,4'-piperidine], Example 23 b, 1.5 g of sodium hydride, 10 g of 2-difluorobenzene and 50 ml of dimethylsulfoxide is stirred at 60° C. under nitrogen for 30 minutes. Thereafter, the mixture is permitted to cool before adding ice-water. The biphasic mixture is extracted thrice with ether. The combined ether extracts are extracted with a large excess of dilute hydrochloric acid. The acidic extract is basified with concentrated ammonium hydroxide effecting a heavy oil. The oil is purified by passing through an alumina column, ether eluant, to provide a yellowish oil. The oil, in ether, is converted to its maleic acid salt which is recrystallized from an acetone-ether mixture providing off-white crystals, mp 166°–168° C. of 6-chloro-1-(2-fluorophenyl)-1'-methylspiro[indoline-3,4'-piperidine]maleate.

Analysis: Calculated for $C_{19}H_{20}ClFN_2 \cdot C_4H_4O_4$: 61.81%C; 5.41%H; 6.27%N; 4.25%F. Found: 62.26%C; 5.48%H; 6.30%N; 4.47%F.

EXAMPLE 26

A sample of 6-chloro-1-(2-fluorophenyl)-1'-methylspiro[indoline-3,4'-piperidine], free base of Example 25, is treated according to the method of Example 25 to provide 6-chloro-1'-cyano-1-(2-fluorophenyl)spiro[indoline-3,4'-piperidine].

EXAMPLE 27

A solution of 3.4 g of 6-chloro-1'-cyano-1-(2-fluorophenyl)spiro[indoline-3,4'-piperidine], Example 26, in 50 ml of tetrahydrofuran is added dropwise to a refluxing slurry of 1.0 g of lithium aluminum hydride in 50 ml of tetrahydrofuran. After total addition the mixture is stirred at reflux for 2.5 hours before being treated with water and alkali. The resulting oily product, in ether, is converted to its maleic acid salt which is recrystallized from an ethyl alcohol-ether mixture to provide off-white granules, mp 174.5°–175.5° C. of 6-chloro-1-(2-fluorophenyl)spiro[indoline-3,4'-piperidine] meleate.

Analysis: Calculated for $C_{18}H_{18}ClFlN_2 \cdot C_4H_4O_4$: 61.03%C; 5.12%H; 6.47%N; 8.19%Cl. Found: 61.33%C; 5.35%H; 6.51%N; 7.84%Cl.

EXAMPLE 28

A mixture of 2.4 g of 6-chloro-1'-methylspiro[indoline-3,4'-piperidine], Example 23 b, 0.5 g of sodium hydride (99%) and 6 g of 2-chlorofluorobenzene in 25 ml of dimethylsulfoxide is stirred at 45° C. under nitrogen for 1 hour. Thereafter, the mixture is quenched with ice-water before being extracted thrice with ether. The combined ether extracts are successively washed with water, dried and concentrated under vacuum leaving a reddish oil. The oil is passed through an alumina column, ether eluant, and the purified oil, in ether, is converted to its maleic acid salt. The salt is recrystallized from an acetone-ether mixture to provide off-white platelets, mp 172°–173° C. of 6-chloro-1-(2-chlorophenyl)-1'-methylspiro[indoline-3,4'-piperidine] maleate.

Analysis: Calculated for $C_{19}H_{20}Cl_2N_2 \cdot C_4H_4O_4$: 59.62%C; 5.22%H; 6.05%N. Found: 59.69%C; 5.25%H; 5.98%N.

EXAMPLE 29

A mixture of 0.8 g of 6-chloro-1-(2-chlorophenyl)-1'-methylspiro[indoline-3,4'-piperidine], free base of Example 28, and 0.5 g of phenyl chloroformate in 20 ml of methylene chloride is stirred at ambient temperature for 16 hours. Thereafter, the mixture is successively washed with 10% sodium hydroxide, washed with water, dried and concentrated under vacuum leaving a brownish oil. The oil is passed through an alumina column, ether eluant, providing a colorless gum of 6-chloro-1-(2-chlorophenyl)-1'-phenoxycarbonylspiro[indoline-3,4'-piperidine]. IR and NMR spectra confirm the assigned structure.

Analysis: Calculated for $C_{25}H_{22}Cl_2N_2O_2$: 66.23%C; 4.89%H; 6.18%N. Found: 66.48%C; 4.87%H; 6.19%N.

EXAMPLE 30

A mixture of 2.4 g of 6-chloro-1'-methylspiro[indoline-3,4'-piperidine], Example 23 b, 5.4 g of 2-fluoronitrobenzene and 1.0 g of sodium bicarbonate is stirred at 160°–165° C. under nitrogen, for 16 hours. Thereafter, the mixture is permitted to cool before sequentially being quenched with water and extracted thrice with ether. The combined ether extracts are shaken with a large excess of 1 N hydrochloric acid. The acidified layer is basified providing a reddish oil which upon drying over magnesium sulfate and then cooling leaves an orange solid. The solid is recrystallized from an etherpentane mixture to provide prisms, mp 130°–131° C. of 6-chloro-1'-methyl-1-(2-nitrophenyl)spiro[indoline-3,4'-piperidine].

Analysis: Calculated for $C_{19}H_{20}ClN_3O_2$: 63.77%C; 5.63%H; 11.74%N. Found: 63.97%C; 5.67%H; 11.77%N.

EXAMPLE 31

A mixture of 3.2 g of 6-chloro-1'-methyl-1-(2-nitrophenyl)spiro[indoline-3,4'-piperidine], Example 30, 2.0 g of cyanogen bromide and 6.0 g of potassium carbonate in 100 ml of chloroform is stirred at ambient temperature for 6 hours. Thereafter, the mixture is sequentially quenched with water, extracted with dilute sodium hydroxide and dried. The chloroform is removed under reduced pressure and the residue is passed through a silica gel column, ether eluant, providing an orange oil which crystallizes upon standing. The solid is recrystallized from an acetone-hexane mixture to provide orange prisms, mp 163°–165° C. of 6-chloro-1'-cyano-1-(2-nitrophenyl)spiro[indoline-3,4'-piperidine].

Analysis: Calculated for $C_{19}H_{17}ClN_4O_2$: 61.87%C; 4.65%H; 15.19%N. Found: 62.14%H; 4.70%H; 15.54%N.

EXAMPLE 32

A sample of 1.5 g of 6-chloro-1'-methyl-1-(2-nitrophenyl)spiro[indoline-3,4'-piperidine], Example 30, is treated according to the procedure of Example 30 to an orange solid, mp 181°–182.5° C. of 6-chloro-1-(2-nitrophenyl)-1'-phenoxycarbonylspiro[indoline-3,4-piperidine], chromatography eluant is methylene chloride, after three recrystallizations from an acetone-pentane mixture and drying at 100° C.

Analysis: Calculated for $C_{25}H_{22}ClN_3O_4$: 64.72%C; 4.78%H; 9.06%N. Found: 64.97%C; 4.72%H; 9.19%N.

EXAMPLE 33

A suspension of 2.5 g of 6-chloro-1'-cyano-1-(2-nitrophenyl)spiro[indoline-3,4'-piperidine], Example 31, in 40 ml of 3 N hydrochloric acid and 20 ml of glacial acetic acid is refluxed for 16 hours under nitrogen. Thereafter, the mixture is permitted to cool before sequentially being basified with dilute sodium hydroxide and extracted with ether. The combined ether extracts are successively washed with water, dried and concentrated under vacuum leaving an oil residue. The residue, in ether, is converted to its maleic acid salt which is recrystallized from an acetone-ether mixture to provide orange prisms, mp 153°–155° C. of 6-chloro-1-(2-nitrophenyl)spiro[indoline-3,4'-piperidine] maleate.

Analysis: Calculated for $C_{18}H_{18}ClN_3O_2 \cdot C_4H_4O_4$: 57.45%C; 4.82%H; 9.14%N; 7.71%Cl. Found: 57.19%C; 4.65%H; 9.12%N; 7.73%Cl.

EXAMPLE 34

A mixture of 2.1 g of 6-chloro-1-(2-nitrophenyl)-spiro[indoline-3,4'-piperidine], free base of Example 33, 95 ml of 95% ethyl alcohol, 7.5 ml of water and 4.4 g of iron powder is acidified with 0.2 ml of concentrated hydrochloric acid and then refluxed under nitrogen for 10 minutes. Thereafter, the mixture is permitted to cool before being filtered through celite. The filtrate is concentrated under vacuum leaving an oily residue which is basified. The alkaline mixture is extracted with ether and then dried. The product is converted to a solid dihydrochloric acid salt which is recrystallized from a methyl alcohol-ether mixture to provide off-white prisms, mp 270°–273° C. (after darkening) of 1-(2-aminophenyl)-6-chlorospiro[indoline-3,4'-piperidine]-dihydrochloride.

Analysis: Calculated for $C_{18}H_{20}ClN_3 \cdot 2HCl$: 55.90%C; 5.73%H; 10.86%N. Found: 56.13%C; 5.53%H; 10.62%N.

EXAMPLE 35

A sample of 2.5 g of 6-chloro-1'-methyl-1-(2-nitrophenyl)spiro[indoline-3,4'-piperidine], Example 30, is treated according to the procedure of Example 35, to provide off-white granules, mp>245° C. (slowly decomposed) of 1-(2-aminophenyl)-6-chloro-1'-methylspiro[indoline-3,4'-piperidine]dihydrochloride, from a methyl alcohol-acetone-ether mixture.

Analysis: Calculated for $C_{19}H_{22}ClN_3 \cdot 2HCl$: 56.94%C; 6.04%H; 10.48%N. Found: 57.06%C; 6.05%H; 10.54%N.

EXAMPLE 36

To a mixture of 15.0 g of 1-(2-aminophenyl)-1'-methylspiro-[indoline-3,4'-piperidine]dihydrochloride, Example 16, in 75 ml of dimethylformamide at 90° C. under nitrogen is added 8.6 g of sodium methoxide. Following this addition the reaction temperature is increased to 110°–115° C. and maintained at this temperature for 40 minutes. The resulting dark brown mixture is permitted to cool to 90° C. and then poured onto 800 ml of ice-water. The mixture is filtered and the filter cake is washed with water and then dissolved in chloroform. The chloroform solution is successively washed with brine, dried and concentrated leaving a red colored glass. The glass is dissolved in ether, where it is converted to its hydrochloric acid salt which is collected by filtration and then washed with ether and finally dried. The salt is recrystallized from a methyl alcohol-ether mixture to provide the product, mp 287.5° C., dec of 1-(2-formamidophenyl)-1'-methylspiro[indoline-3,4'-piperidine]hydrochloride.

Analysis: Calculated for $C_{20}H_{23}N_3O \cdot HCl$: 67.12%C; 6.76%H; 11.74%N. Found: 67.08%C; 6.77%H; 11.53%N.

We claim:
1. A compound of the formula

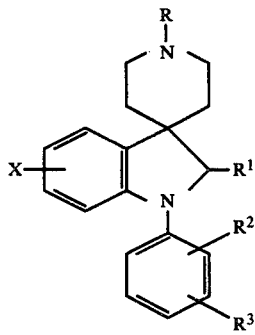

in which R is hydrogen, loweralkyl, cyano, loweralkanoyl, phenoxycarbonyl, phenylloweralkyl, phenylloweralkanoyl, loweralkenyl, cycloalkylloweralkyl, in which the cycloalkyl moiety contains 3 to 8 carbon atoms, benzoyl,

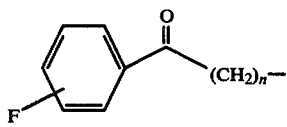

or ethylene glycol ketal of the formula

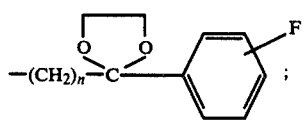

$R^1$ is hydrogen or loweralkyl; $R^2$ and $R^3$ are the same or different and each can be hydrogen, halogen, trifluoromethyl, loweralkyl, loweralkoxy, hydroxy, nitro, amino, formamido or acetamido; X is hydrogen, halogen, loweralkyl, loweralkoxy or hydroxy; n is an integer from 1 to 4; and a physiologically acceptable salt thereof.

2. A compound as defined in claim 1 in which R is loweralkyl, hydrogen, cycloalkylloweralkyl in which the cycloalkyl moiety contains 3 to 8 carbon atoms or

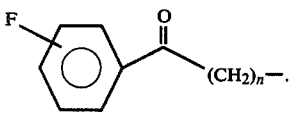

3. A compound as defined in claim 2 in which $R^3$ and X are each hydrogen.

4. A compound as defined in claim 1 in which $R^1$ is hydrogen or loweralkyl.

5. A compound as defined in claim 4 in which R is methyl or hydrogen.

6. A compound as defined in claim 5 in which $R^3$ is hydrogen and X is hydrogen or halogen.

7. The compound defined in claim 1 which is 1'-methyl-1-(4-trifluoromethylphenyl)spiro[indoline-3,4'-piperidine].

8. The compound defined in claim 1 which is 1-(4-chlorophenyl)-1'-methylspiro[indoline-3,4'-piperidine].

9. The compound defined in claim 1 which is 1'-methyl-1-phenylspiro[indoline-3,4'-piperidine].

10. The compound defined in claim 1 which is 1-(4-fluoro-phenyl)-1'-methylspiro[indoline-3,4'-piperidine].

11. The compound defined in claim 1 which is 1-(2-chlorophenyl)-1'-methylspiro[indoline-3,4'-piperidine].

12. The compound defined in claim 1 which is 1'-[3-(4-fluorobenzoyl)propyl]-1-(4-fluorophenyl)spiro[indoline-3,4'-piperidine].

13. The compound defined in claim 1 which is 1-(4-fluorophenyl)spiro[indoline-3,4'-piperidine].

14. The compound defined in claim 1 which is 1-(2-nitrophenyl)-1'-methylspiro[indoline-3,4'-piperidine].

15. The compound defined in claim 1 which is 1-(2-aminophenyl)-1'-methylspiro[indoline-3,4'-piperidine].

16. A compound defined in claim 1 which is 1-(2-acetylaminophenyl)-1'-methylspiro[indoline-3,4'-piperidine]oxalate.

17. A compound defined in claim 1 which is 1-(2-formamidophenyl)-1'-methylspiro[indoline-3,4'-piperidine]hydrochloride.

18. A compound defined in claim 1 which is 6-chloro-1-(2-fluorophenyl)-1'-methylspiro[indoline-3,4'-piperidine] maleate.

19. A compound defined in claim 1 which is 6-chloro-1'-methyl-1-(2-nitrophenyl)spiro[indoline-3,4'-piperidine].

20. A compound defined in claim 1 which is 6-chloro-1-(2-trifluoromethylphenyl)-1'-methylspiro[indoline-3,4'-piperidine] maleate.

21. A compound defined in claim 1 which is 6-chloro-1-(2-chlorophenyl)-1'-methylspiro[indoline-3,4'-piperidine]maleate.

22. A compound defined in claim 1 which is 6-chloro-1-(2-fluorophenyl)spiro[indoline-3,4'-piperidine] maleate.

23. A compound defined in claim 1 which is 1-(2-aminophenyl)6-chloro-1'-methylspiro[indoline-3,4'-piperidine] dihydrochloride.

24. The compound defined in claim 1 which is 6-chloro-1-(2-nitrophenyl)spiro[indoline-3,4'-piperidine] maleate.

25. A compound defined in claim 1 which is 1-(2-aminophenyl)6-chlorospiro[indoline-3,4'-piperidine] dihydrochloride.

26. A method of treating depression which comprises administering to a patient in need of such treatment a pharmaceutically effective amount of a compound defined in claim 1.

27. A method of treating convulsions which comprises administering to a patient in need of such treatment a pharmaceutically effective amount of a compound defined in claim 1.

28. A method of tranquilizing which comprises administering to a patient in need of such tranquilizing a pharmaceutically effective amount of a compound defined in claim 1.

29. A pharmaceutical composition for the treatment of depression and convulsions and for tranquilization which comprises between 0.5 and about 70% by weight defined in claim 1 and a pharmaceutically acceptable carrier therefor.

* * * * *

UNITED STATES PATENT AND TRADEMARK OFFICE
CERTIFICATE OF CORRECTION

PATENT NO. : 4,209,625

DATED : June 24, 1980

INVENTOR(S) : Ong et al.

It is certified that error appears in the above-identified patent and that said Letters Patent are hereby corrected as shown below:

Column 8, line 9, change "antipresant" to --antidepressant--.

Column 8, line 29, change "...methylspiroindoline..." to --...methylspiro[indoline...--.

Column 10, lines 20 and 50, Column 14, line 58 and Column 16, line 55, change "2 N" to --2N--.

Column 15, line 49, change "3 N" to --3N--.

Column 15, line 67, change "...spiro-[indoline..." to--...spiro[indoline...--.

Column 16, line 26, change "with 2200 ml" to --with 2 200 ml--.

Column 17, line 40, change "...3,4'-piperidine)]" to --... 3,4'-piperidine]--.

Column 17, line 46, change "rovide" to --provide--.

Column 19, line 10, change "1 N" to --1N--.

Column 19, line 14, change "etherpentane" to --ether-pentane--.

Column 20, line 42, change "...methylspiro-[indoline...' to --...methylspiro[indoline...--.

UNITED STATES PATENT AND TRADEMARK OFFICE
CERTIFICATE OF CORRECTION

PATENT NO. : 4,209,625
DATED : June 24, 1980
INVENTOR(S) : Ong et al.

It is certified that error appears in the above-identified patent and that said Letters Patent are hereby corrected as shown below:

Claim 10, change "...fluoro-phenyl)-..." to --...fluorophenyl)-...--.

Claim 23 and 25, change "...phenyl)6-chloro..." to --...phenyl)-6-chloro...--.

Claim 24, change "The compound" to --A compound--.

Claim 29, insert --of a compound-- between "by weight" and "defined in Claim 1".

Signed and Sealed this

Third Day of February 1981

[SEAL]

Attest:

RENE D. TEGTMEYER

Attesting Officer    Acting Commissioner of Patents and Trademarks